United States Patent [19]

Hlavka et al.

[11] Patent Number: 4,577,018

[45] Date of Patent: Mar. 18, 1986

[54] 2,3-DIAMINO-SUBSTITUTED-4(3H)-PYRIMIDINONES AND PLATINUM CHELATES

[75] Inventors: Joseph J. Hlavka, Tuxedo; Panayota Bitha, Pomona; Yang-i Lin, Nanuet, all of N.Y.

[73] Assignee: American Cyanamid Company, Stamford, Conn.

[21] Appl. No.: 525,531

[22] Filed: Aug. 22, 1983

[51] Int. Cl.[4] .................... C07F 15/00; C07D 471/14; C07D 471/04; C07D 487/04

[52] U.S. Cl. ..................... 544/225; 544/250; 544/251; 544/279; 544/253; 544/320; 544/321

[58] Field of Search .......... 544/225; 424/245

[56] References Cited

U.S. PATENT DOCUMENTS 4,419,351 12/1983 Rosenberg et al. .

Primary Examiner—Mark L. Berch
Attorney, Agent, or Firm—Edward A. Conroy, Jr.

[57] ABSTRACT

Platinum chelates of 2,3-diamino-substituted-4(3H)-pyrimidinones which are useful as antitumor agents.

15 Claims, No Drawings

2,3-DIAMINO-SUBSTITUTED-4(3H)-PYRIMIDINONES AND PLATINUM CHELATES

SUMMARY OF THE INVENTION

This invention relates to platinum chelates of new organic compounds and, more particularly, is concerned with platinum chelates of 2,3-diamino-substituted-(3H)-pyrimidinones which are useful as antitumor agents and which may be represented by the following formula I:

FORMULA I

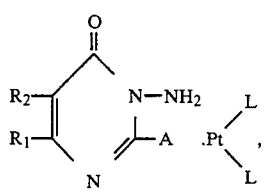

wherein $R_1$ is selected from the group consisting of straight or branched chain alkyl($C_1$-$C_6$), trifluoromethyl, phenyl, p-chlorophenyl and p-nitrophenyl; $R_2$ is selected from the group consisting of hydrogen, alkyl($C_1$-$C_4$); halogen, benzyl and hydroxyethyl; $R_1$ and $R_2$ taken together are selected from the group consisting of —$(CH_2)_n$—, where n is 3-6,

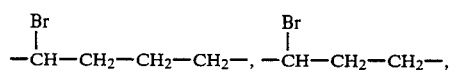

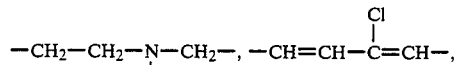

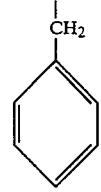 and 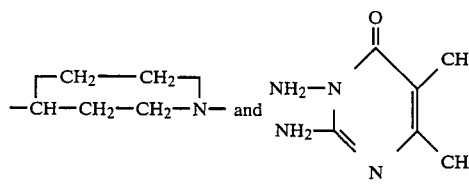

A is selected from the group consisting of —$NH_2$ and —$NHNH_2$; and L and L' are the same and are selected from the group consisting of halide, nitrate, nitrite, sulfate and a monobasic organic acid, such as glucuronic acid, or L and L' taken together may be a dibasic organic acid such as malonic acid, oxalic acid, methyl malonic acid, succinic acid, or tartronic acid.

In addition this invention is concerned with a class of intermediates used to prepare the compounds of formula I, which intermediates may be represented by the following formula II:

FORMULA II

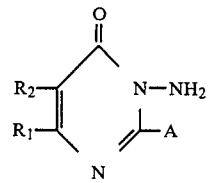

wherein $R_1$, $R_2$, and A are as described hereinabove.

DESCRIPTION OF THE INVENTION

The novel compounds of the present invention are prepared in accordance with the following reaction scheme:

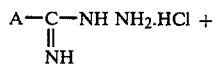

(1)

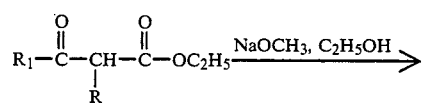

(2)

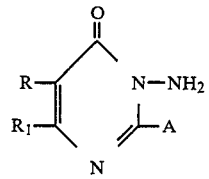

(3)

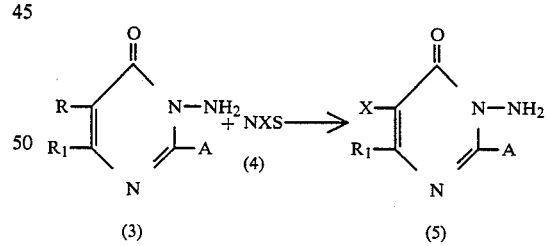

(when R=H)

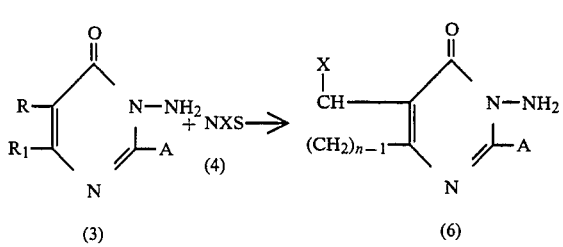

[when R and $R_1$ = —$(CH_2)_n$—]

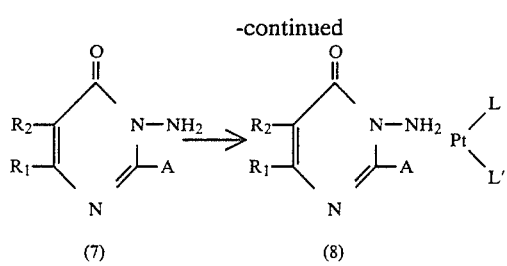

(where R₂ is as defined above)
where $R_1$ and $R^2$ are as hereinabove defined; R is selected from the group consisting of hydrogen, alkyl($C_1$-$C_4$), benzyl and hydroxyethyl; R and $R_1$ taken together are selected from the group consisting of —$(CH_2)_n$—(wherein=3-6),

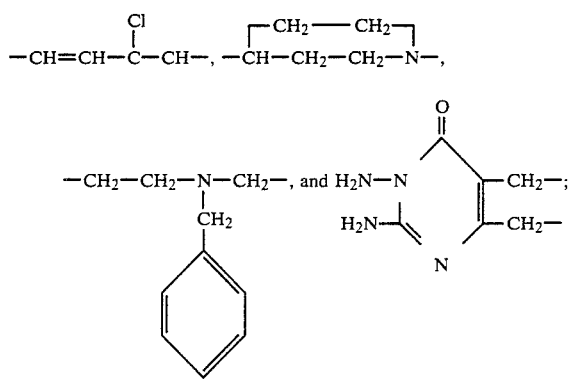

A is —$NH_2$ or —$NHNH_2$ and X is halogen.

In accordance with the above reaction scheme, aminoguanidine hydrochloride of N,N'-diaminoguanidine hydrochloride (1) is reacted with sodium methoxide in ethanol for 10-30 minutes, filtered and then reacted with a β-keto ester (2) with stirring at room temperature overnight, giving the 2,3-diamino(or 2-hydrazino-3-amino)-substituted-4(3H)-pyrimidinone (3). This pyrimidinone (3) may then be treated with an N-halosuccinimide (4) in glacial acetic acid at 20°-120° C. for 1-3 hours, then precipitated in ether, giving either the 2,3-diamino(or 2-hydrazino-3-amino)disubstituted-4(3H)-pyrimidinone (5) when R is hydrogen or (6) when R and $R_1$ taken together are —$(CH_2)_n$ (where n is 3-6). Pyrimidinones (7) are then dissolved in a mixture of methanol, ethanol, water and dimethylformamide and treated with an aqueous solution of platinum chloride, giving the products (8).

To prepare compounds of formula I where L and L' are nitro, compounds of formula I where L and L' are chloro are dissolved in water and reacted with 2 equimolar amounts of silver nitrate for several hours at room temperature, then filtered and the filtrate evaporated to give the dinitrate derivatives.

To obtain the organic acid derivatives the dinitrate compound is reacted with one equimolar amount of the potassium salt of a dibasic acid or 2 equimolar amounts of the potassium salt of a monobasic acid.

The novel chelated compounds of the present invention possess the property of inhibiting the growth of transplanted mouse tumors as established by the following test.

Lymphocytic leukemia P388 test

The animals used were BDF/1 mice all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1,5 and 9, relative to tumor inoculation, at various doses. The animals were weighed and survivors recorded on a regular basis for 30 days. The median survival time and the ratio of survival time for treated (T)/control (C) animals were calculated. The positive control compound was either 1,4-dihydroxy-5,8-bis[[2-(2-hydroxyethylamino)ethyl]amino]anthraquinone dihydrochloride or Cisplatin. The results of this test on representative compounds of this invention appear in Table I.

TABLE I

| Compound | Dose (mg/kg)/ (Days) | Median Survival (%) | T/C × 100 |
|---|---|---|---|
| 2,3-diamino-5,6,7,8-tetrahydro-1,3-benzotriazin-4(3H)—one, compound with platinum chloride (1:1) | 400 | 13.5 | 135 |
| | 200 | 13.5 | 135 |
| | 100 | 14 | 140 |
| | 50 | 13 | 130 |
| Control | — | 10 | — |
| 1,4-dihydroxy-5,8-bis[[2-(2-hydroxyethylamino)ethyl]amino]anthraquinone dihydrochloride (Hereinafter called Positive Control) | 1.6 | >30 | >300 |
| | 0.4 | 27 | 270 |
| | 0.1 | 18 | 180 |
| | 0.025 | 12.5 | 125 |
| 2,3-diamino-6-(4-nitrophenyl)-4(3H)—pyrimidinone, compound with platinum chloride (1:1) | 200 | 14 | 147 |
| Control | — | 9.5 | — |
| Positive Control | 1.6 | >30 | >316 |
| | 0.4 | 21.5 | 226 |
| | 0.1 | 17.5 | 184 |
| | 0.025 | 15 | 156 |
| 2,3-diamino-5,6-dimethyl-4(3H)—pyrimidinone, compound with platinum chloride (1:1) | 50 | 16.5 | 174 |
| | 12 | 14 | 147 |
| | 3 | 13.5 | 142 |
| Control | — | 9.5 | — |
| Positive Control | 1.6 | >30 | >316 |
| | 0.4 | 21.5 | 226 |
| | 0.1 | 17.5 | 184 |
| | 0.025 | 15 | 156 |
| 2,3-diamino-6-methyl-4(3H)—pyrimidinone, compound with platinum chloride (1:1) | 200 | 15.5 | 129 |
| Control | — | 12 | — |
| Cisplatin | 12 | 5.5 | 46 |
| | 6 | 7.5 | 63 |
| | 3 | 12 | 100 |
| | 1.5 | 25.5 | 213 |
| 2,3-diamino-3,5,6,7-tetrahydro-4H—cyclopentapyrimidinone, compound with platinum chloride (1:1) | 50 | 18 | 171 |
| | 12 | 15 | 143 |
| | 3 | 13.5 | 129 |
| Control | — | 10.5 | — |
| Positive Control | 1.6 | 21.5 | 205 |
| | 0.4 | >29 | >276 |
| | 0.1 | 24 | 229 |
| | 0.025 | 17.5 | 167 |
| 2,3-diamino-5-bromo-6-methyl-4(3H)—pyrimidinone, compound with platinum chloride (1:1) | 16 | 17 | 138 |
| | 4 | 16.5 | 134 |
| | 1 | 17.5 | 167 |
| Control | — | 11.2 | — |
| Cisplatin | 2 | 20.5 | 183 |
| | 1 | 17 | 152 |
| | 0.5 | 14.5 | 129 |
| 3-amino-2-hydrazino-5,6-dimethyl-4(3H)—pyrimidinone, compound with platinum chloride (1:1) | 200 | 14.5 | 138 |
| | 50 | 14 | 133 |
| Control | — | 10.5 | — |

TABLE I-continued

| Compound | Dose (mg/kg)/(Days) | Median Survival (%) | T/C × 100 |
|---|---|---|---|
| Positive Control | 1.6 | 21.5 | 205 |
| 2,3-diamino-5-bromo-6-phenyl-4(3H)—pyrimidinone, compound with platinum chloride (1:1) | 50 | 15 | 140 |
| Control | — | 10.7 | — |
| Cisplatin | 2.5 | 16 | 150 |
|  | 1.2 | 22 | 206 |
|  | 0.6 | 21 | 192 |
| 2,3-diamino-8-bromo-5,6,7,8-tetrahydro-4(3H)—pyrimidinone, compound with platinum chloride (1:1) | 100 | 18 | 180 |
|  | 50 | 13.5 | 135 |
|  | 25 | 13 | 130 |
| Control | — | 10 | — |
| Cisplatin | 3 | 13 | 130 |
|  | 1.5 | 10.5 | 105 |
| 2,3-diamino-5,6,7,8-tetrahydro-6-(phenylmethyl)-pyrido[4,3-d]pyrimidin-4(3H)—one, compound with platinum chloride (1:1) | 200 | 19 | 146 |
| Control | — | 13 | — |
| Cisplatin | 3 | 30 | 231 |
| 2,3-diamino-6-(trifluoromethyl)-4(3H)—pyrimidinone compound with platinum chloride (1:1) | 50 | 20 | 169 |
|  | 12 | 18 | 153 |
|  | 3 | 15 | 127 |
| Control | — | 11.8 | — |
| Cisplatin | 2 | 20.5 | 183 |
|  | 1 | 17 | 152 |
|  | 0.5 | 14.5 | 129 |
| 2,3-diamino-6-(1-methylethyl)-4(3H)—pyrimidinone, compound with platinum chloride (1:1) | 200 | 2.15 | 215 |
|  | 50 | 19.5 | 195 |
|  | 12 | 13.5 | 135 |
|  | 3 | 13 | 130 |
| Control | — | 10 | — |
| Cisplatin | 2 | 12 | 120 |
|  | 1 | 21.5 | 215 |
|  | 0.5 | 19 | 190 |
| 2,3-diamino-7,8-dihydro-3H—5,8-ethanopyrido[3,2-d]-pyrimidin-4(6H)—one, compound with platinum chloride (1:1) | 200 | 19.5 | 150 |
|  | 50 | 18 | 138 |
| Control | — | 13 | — |
| Cisplatin | 3 | >30 | >231 |
| 3-amino-2-hydrazino-6-n-propyl-4(3H)—pyrimidinone, compound with platinum chloride (1:1) | 200 | 12 | 120 |
|  | 50 | 11 | 110 |
| Control | — | 10 | — |
| Cisplatin | 0.8 | 23.5 | 235 |
|  | 0.2 | 21 | 210 |
| 2,3-diamino-5-(2-hydroxyethyl)-6-methyl-4(3H)pyrimidinone, compound with platinum chloride (1:1) | 200 | 19 | 190 |
|  | 50 | 18 | 180 |
|  | 12 | 16.5 | 165 |
|  | 3 | 13 | 130 |
| Control | — | 10 | — |
| Cisplatin | 0.8 | 23.5 | 235 |
|  | 0.2 | 21 | 210 |
| 2,3-diamino-6-propyl-4(3H)—pyrimidinone, compound with with platinum chloride (1:1) | 200 | 15 | 147 |
|  | 50 | 13 | 127 |
| Control | — | 10.2 | — |
| Cisplatin | 1.25 | 13.5 | 132 |
|  | 0.6 | 22.5 | 221 |
| 2,3-diamino-6-(4-chlorophenyl)-4(3H)—pyrimidinone, compound with platinum chloride (1:1) | 25 | 14 | 127 |
| Control | — | 11 | — |
| Cisplatin | 1.25 | 14.5 | 138 |
|  | 0.6 | 15.5 | 148 |
| 2,3-diamino-5-iodo-6-methyl-4(3H)—pyrimidinone, compound with platinum chloride (1:1) | 200 | 11.5 | 110 |
|  | 50 | 11 | 105 |
|  | 12 | 11 | 105 |
| Control | — | 10.5 | — |
| Cisplatin | 1.25 | 14.5 | 138 |
|  | 0.6 | 15.5 | 148 |

This aspect of the invention includes the novel compositions of matter and the method of inducing the regression and/or palliation of leukemia and related cancers in mammals when administered in amounts ranging from about one mg to about 1.2 gm per square meter of body surface area per day. The interrelationship of dosages for animals of various sizes and species and humans (based on mg/m$^2$ of surface area) is descibed by Freireich, E. J., et al., Quantitative Comparison of Toxicity of Anticancer Agents in Mouse, Rat, Hamster, Dog, Monkey and Man. Cancer Chemother. Rep., 50, No. 4, 219–244, May 1966. A preferred dosage regimen for optimum results would be from about 3 mg/m$^2$/day to about 200 mg/m$^2$/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micoorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compostions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This treatment will be described in greater detail in conjunction with the following specific examples.

EXAMPLE 1

2,3,-Diamino-3,5,6,7-tetrahydro-4H-cyclopentapyrimidin-4-one

A mixture of 11.0 g of aminoguanidine hydrochloride and 5.4 g of sodium methoxide in 100 ml of absolute ethanol was stirred for 20 minutes and then filtered. To the filtrate was added 7.8 g of ethyl 2-oxocyclopentane carboxylate providing an exothermic reaction. This mixture was stirred overnight, then the solid was collected, washed with ethanol and ether and dried at 60° C. in vacuo, giving 2.6 g of the desired intermediate, mp 246°-248° C.

Following the procedure of Example 1, but using appropriate acetate starting materials and aminoguanidine hydrochloride or N,N'-diaminoguanidine hydrochloride, the intermediates of Examples 2-18, listed in Table II were obtained.

TABLE II

| Example | Acetate | Intermediate | MP °C. |
|---|---|---|---|
| 2 | ethylacetoacetate | 2,3-diamino-6-methyl-4(3H)—pyrimidinone | 282–285 |
| 3 | ethyl-2-methylacetoacetate | 2,3-diamino-5,6-dimethyl-4(3H)—pyrimidinone | 220–225 |
| 4 | ethyl-p-nitrobenzoylacetate | 2,3-diamino-6-(4-nitrophenyl)-4(3H)—pyrimidinone | 235–250 |
| 5 | 1-benzyl-3-carbethoxy-4-piperidone hydrochloride | 2,3-diamino-5,6,7,8-tetrahydro-6-(phenylmethyl)-pyrido[4,3-d]pyrimidinone 4(3H)—one | 270–272 |
| 6 | ethyl-2-methylacetoacetate | 3-amino-2-hydrazino-5,6-dimethyl-4(3H)—pyrimidinone | 137–140 |
| 7 | ethyl butyrylacetate | 2,3-diamino-6-n-propyl-4(3H)—pyrimidinone | 148–150 |
| 8 | ethyl-p-chlorobenzoylacetate | 2,3-diamino-6-(4-chlorophenyl)-4(3H)—pyrimidinone | 238–242 |
| 9 | ethyl isobutyrylacetate | 2,3-diamino-6-(1-methylethyl)-4(3H)—pyrimidinone | 158–160 |
| 10 | ethyl 2-benzylacetoacetate | 2,3-diamino-6-methyl-5-(phenylmethyl)-4(3H)—pyrimidinone | 224–226 |
| 11 | ethyl 2-n-propylacetoacetate | 2,3-diamino-6-methyl-5n-propyl-4(3H)—pyrimidinone | 260 (dec) |

TABLE II-continued

| Example | Acetate | Intermediate | MP °C. |
|---|---|---|---|
| 12 | ethyl propionylacetate | 2,3-diamino-6-ethyl-4(3H)—pyrimidinone | 177–179 |
| 13 | methyl 4,4-dimethyl-3-oxo-valerate | 2,3-diamino-6-(1,1-dimethyl-ethyl)-4(3H)—pyrimidinone | 165–167 |
| 14 | ethyl 2-ethylacetoacetate | 2,3-diamino-5-ethyl-6-methyl-4(3H)—pyrimidinone | 213–215 |
| 15 | ethyl α-ethylbenzoyl-acetate | 2,3-diamino-5-ethyl-6-phenyl-4(3H)—pyrimidinone | 170–173 |
| 16 | ethyl 4-chlorosalicylate | 2,3-diamino-6-chloro-4(3H)—quinazoline | 130–132 |
| 17 | ethyl-3-bromo-2-cyclo-pentane carboxylate | 2,3-diamino-7-bromo-3,5,6,7-tetrahydro-4H—cyclopenta-pyrimidin-4-one | 87–90 |
| 18 | ethyl butyrylacetate | 3-amino-2-hydrazino-6-n-propyl-4(3H)—pyrimidinone | 155–157 |

EXAMPLE 19

2,3-Diamino-8-bromo-5,6,7,8-tetrahydro-4(3H)-quinazoline

A solution of 1.0 g of 2,3-diamino-5,6,7,8-tetrahydro-1,3-benzotriazin-4(3H)-one, 979 mg of N-bromosuccinimide and 9 ml of glacial acetic acid was stirred at room temperature. The solid was collected, washed with ether, dried and slurried in 20 ml of boiling water. This mixture was stirred 30 minutes while hot, then the solid was collected and dried, giving the desired intermediate, mp 150°–155° C.

Following the procedure of Example 19, but using different pyrimidinone starting materials and appropriate succinimide derivatives, the intermediates of Examples 20–22, listed in Table III, were obtained.

TABLE III

| Example | Pyrimidinone | Intermediate | MP °C. |
|---|---|---|---|
| 20 | 2,3-diamino-6-methyl-4(3H)—pyrimidinone | 2,3-diamino-5-bromo-6-methyl-4(3H)—pyrimidinone | 245–248 |
| 21 | 2,3-diamino-6-phenyl-4(3H)—pyrimidinone | 2,3-diamino-5-bromo-6-phenyl-4(3H)—pyrimidinone | 280–282 |
| 22 | 2,3-diamino-6-methyl-4(3H)—pyrimidinone | 2,3-diamino-5-iodo-6-methyl-4(3H)—pyrimidinone | 230–232 |

EXAMPLE 23

2,3-diamino-6-(trifluoromethyl)-4(3H)-pyrimidinone

A 40.8 g portion of aminoguanidine carbonate was slurried in 250 ml of n-butanol and then refluxed for 15 minutes. A 55.2 g portion of ethyl 4,4,4-trifluoroacetylacetate was added, the mixture was refluxed 5 hours and then filtered while hot. The filtrate was cooled in an ice bath and the solid collected and dried, given 26 g of the desired intermediate, mp 215°–218° C.

EXAMPLE 24

2,3-Diamino-5,6,7,8-tetrahydro-1,3-benzotriazin-4(3H)-one

A mixture of 17.0 g of ethyl 2-cyclohexanecarboxylate and 13.6 g of aminoguanidine carbonate in 100 ml of n-butanol was heated at reflux for 4.5 hours. The resulting solid was collected, giving 15 g of the desired intermediate, mp 215°–220° C.

EXAMPLE 25

2,3-Diamino-5-(2-hydroxyethyl)-6-methyl-4(3H)-pyrimidinone

A mixture of 13.6 g of aminoguanidine bicarbonate and 12.8 g of 2-acetyl butyrolactone in 80 ml of n-butanol was heated at reflux until a clear solution was obtained. This solution was cooled, evaporated to dryness in vacuo and the residue was triturated with 200 ml of a 50/50 ether-chloroform mixture, giving 12 g of the desired intermediate, mp 126°–135° C.

EXAMPLE 26

2,3,7,8-tetraamino-3,5,8,10-tetrahydropyrimido[4,5-g]quinazoline-4,9-dione

A mixture of 12.8 g of diethyl 1,4-cyclohexanedione-2,5-dicarboxylate and 13.6 g of aminoguanidine aminoguanidine bicarbonate in 100 ml of n-butanol was heated at reflux for 9 hours. Cooling produced 17 g of the desired intermediate, mdesired intermediate, mp>300° C.

EXAMPLE 27

2,3-Diamino-6-(4-nitrophenyl)-4(3H)-pyrimidinone, compound with platinum chloride (1:1)

A suspension of 494.4 mg of 2,3-diamino-6-(4-nitrophenyl)-4(3H)-pyrimidinone in 20 ml of dimethylformamide was mixed with a solution of 930 mg of potassium tetrachloroplatinate in 20 ml of water. The suspension was stirred overnight and then filtered. The filtrate was evaporated to dryness and the residue washed with water and dried, giving the desired product, mp 255° C.(dec.).

Following the procedure of Example 27, but using the intermediates of Examples 1–26 and either methanol or dimethylformamide as solvent the products of Examples 28–52, listed in Table IV were obtained.

TABLE IV

| Example | Intermediate of Example | Product | MP °C. |
|---|---|---|---|
| 28 | 3 | 2,3-diamino-5,6-dimethyl-4(3H)—pyrimidinone, compound with platinum chloride (1:1) | >330 |
| 29 | 2 | 2,3-diamino-6-methyl-4(3H)—pyrimidinone, | >300 |

TABLE IV-continued

| Example | Intermediate of Example | Product | MP °C. |
|---|---|---|---|
| 30 | 1 | compound with platinum chloride (1:1) 2,3-diamino-3,5,6,7-tetrahydro-4H—cyclopentapyrimidin-4-one, compound with platinum chloride (1:1) | >250 |
| 31 | 20 | 2,3-diamino-5-bromo-6-methyl-4(3H)—pyrimidinone, compound with platinum chloride (1:1) | >300 |
| 32 | 6 | 3-amino-2-hydrazino-5,6-dimethyl-4(3H)—pyrimidinone, compound with platinum chloride (1:1) | >320 |
| 33 | 21 | 2,3-diamino-5-bromo-6-phenyl-4(3H—pyrimidinone compound with platinum chloride (1:1) | >275 |
| 34 | 19 | 2,3-diamino-8-bromo-5,6,7,8-tetrahydro-4(3H)—pyrimidinone, compound with platinum chloride (1:1) | >300 |
| 35 | 5 | 2,3-diamino-5,6,7,8-tetrahydro-6-(phenylmethyl)-pyrido[4,3d]pyrimidin-4(3H)—one with compound platinum chloride (1:1) | >300 |
| 36 | 22 | 2,3-diamino-6-(trifluoromethyl)-4(3H)—pyrimidinone, compound with platinum chloride (1:1) | >275 |
| 37 | 7 | 2,3-diamino-6-n-propyl-4(3H)—pyrimidinone, compound with platinum chloride (1:1) | >290 |
| 38 | 8 | 2,3-diamino-6-(4-chlorophenyl)-4(3H)—pyrimidinone, compound with platinum chloride (1:1) | >300 |
| 39 | 9 | 2,3-diamino-6-(1-methylethyl)-4(3H)—pyrimidinone, compound with platinum chloride (1:1) | >280 |
| 40 | 24 | 2,3-diamino-5,6,7,8-tetrahydro-1,3-benzotriazin-4(3H)—one, compound with platinum chloride (1:1) | >300 |
| 41 | 25 | 2,3-diamino-5-(2-hydroxyethyl)-6-methyl-4(3H)—pyrimidinone, compound with platinum chloride (1:1) | >300 |
| 42 | 10 | 2,3-diamino-6-methyl-5(phenylmethyl)-4(3H)—pyrimidinone, compound with platinum chloride (1:1) | >50 |
| 43 | 11 | 2,3-diamino-6-methyl-5-n-propyl-4(3H)—pyrimidinone, compound with platinum chloride (1:1) | >300 |
| 44 | 12 | 2,3-diamino-6-ethyl-4(3H)—pyrimidinone, compound with platinum chloride (1:1) | >280 |
| 45 | 13 | 2,3-diamino-6-(1,1-dimethylethyl)-4(3H)—pyrimidinone, compound with platinum chloride (1:1) | >260 |
| 46 | 14 | 2,3-diamino-5-ethyl-6-methyl-4(3H)—pyrimidinone, compound with platinum chloride (1:1) | >260 |
| 47 | 15 | 2,3-diamino-5-ethyl-6-phenyl-4(3H)—pyrimidinone, compound with platinum chloride (1:1) | >260 |
| 48 | 16 | 2,3-diamino-6-chloro-4(3H)—quinazoline, compound with platinum chloride (1:1) | >300 |
| 49 | 17 | 2,3-diamino-7-bromo-3,5,6,7-tetrahydro-4H—cyclopentapyrimidin-4-one, compound with platinum chloride (1:1) | >290 |
| 50 | 26 | 2,3,7,8-tetraamino-3,5,8,10-tetrahydro-pyrimido[4,5-g]quinazoline-4,9-dione, compound with platinum chloride (1:2) | >300 |
| 51 | 18 | 3-amino-2-hydrazino-6-n-propyl-4(3H)—pyrimidinone, compound with platinum chloride (1:1) | >300 |
| 52 | 22 | 2,3-diamino-5-iodo-6-methyl-4(3H)—pyrimidinone, compound with platinum chloride (1:1) | >300 |

EXAMPLE 53

2,3-Diamino-7,8-dihydro-3H-5,8-ethanopyrido[3,2-]pyrimidin-4(6H)-one, compound with platinum chloride (1:1)

The procedure of Example 1 was employed using 3-quinuclidinone-2-carboxylate hydrochloride, giving 2.96 g of 2,3-diamino-7,8 -dihydro-3H-5,8-ethanopyrido[3,2-d]-pyrimidin-4(6H)-one.

An 829 mg portion of the above compound was reacted as described in Example 27, giving 530 mg of the desired compound, mp>340° C.

EXAMPLE 54

2,3-Diamino-5,6,7,8-tetrahydro-1,3-benzotriazin-4(3H)-one, compound with potassium nitrate (1:1)

To a suspension of 1 m mole of 2,3-diamino-5,6,7,8-tetrahydro-1,3-benzotriazin-4(3H)-one, compound with platinum chloride (1:1) in 50 ml of water is added 2 m moles of silver nitrate. The mixture is stirred at room temperature for 3 hours and then filtered. The filtrate is evaporated to dryness giving the desired product.

To obtain the organic acid derivative the dinitro dervative is stirred with one molar equivalent of the potassium salt of a dibasic acid or two molar equivalents of the potassium salt of a monobasic acid in an aqueous medium.

We claim:
1. A compound of the formula:

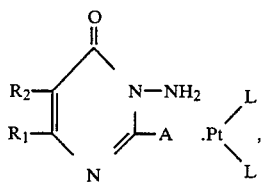

wherein $R_1$ is alkyl($C_1$–$C_6$), trifluoromethyl, phenyl, p-chlorophenyl or p-nitrophenyl; $R_2$ is hydrogen, alkyl($C_1$–$C_4$), halogen, benzyl or hydroxyethyl; $R_1$ and $R_2$ taken together is a divalent moiety selected from the group consisting of —(CH$_2$)$_n$— wherein n is an integer 3–6,

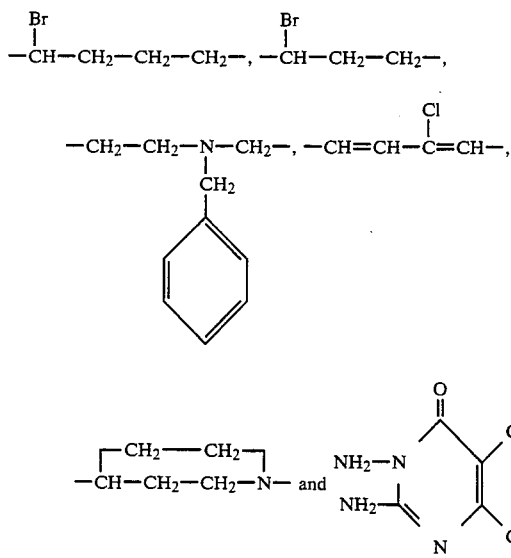

A is amino or hydrazino; and L and L' are the same and are anions selected from the group consisting of halide, nitrate, sulfate and ($C_2$–$C_6$) alkanoate of L and L' taken together is a dibasic anion selected from the group consisting of oxalate, malonate, methylmalonate, succinate, and tartronate.

2. The compound according to claim 1; 2,3-diamino-6-(4-nitrophenyl)-4(3H)-pyrimidinone, compound with platinum chloride (1:1).

3. The compound according to claim 1; 2,3-diamino-5,6-dimethyl-4(3H)-pyrimidinone, compound with platinum chloride (1:1).

4. The compound according to claim 1; 2,3-diamino-6-methyl-4(3H)-pyrimidinone, compound with platinum chloride (1:1).

5. The compound according to claim 1; 2,3-diamino-3,5,6,7-tetrahydro-4H-cyclopentapyrimidinone, compound with platinum chloride (1:1).

6. The compound according to claim 1; 2,3-diamino-5-bromo-6-methyl-4(3H)-pyrimidinone, compound with platinum chloride (1:1).

7. The compound according to claim 1; 3-amino-2-hydrazino-5,6-dimethyl-4(3H)-pyrimidinone, compound with platinum chloride (1:1).

8. The compound according to claim 1; 2,3-diamino-5-bromo-6-phenyl-4(3H)-pyrimidinone, compound with platinum chloride (1:1).

9. The compound according to claim 1; 2,3-diamino-8-bromo-3,5,6,7-tetrahydro-4H-cyclopentapyrimidin-4-one, compound with platinum chloride (1:1).

10. The compound according to claim 1; 2,3-diamino-5,6,7,8-tetrahydro-6-(phenylmethyl)pyrido[4,3-d]pyrimidin-4(3H)-one, compound with platinum chloride (1:1).

11. The compound according to claim 1; 2,3-diamino-6-(trifluoromethyl-4(3H)-pyrimidinone, compound with platinum chloride (1:1).

12. The compound according to claim 1; 2,3-diamino-5-(2-hydroxyethyl)-6-methyl-4(3H)-pyrimidinone, compound with platinum chloride (1:1).

13. The compound according to claim 1; 2,3-diamino-6-propyl-4(3H)-pyrimidinone, compound with platinum chloride (1:1).

14. The compound according to claim 1; 2,3-diamino-6-(1-methylethyl)-4(3H)-pyrimidinone, compound with platinum chloride (1:1).

15. The compound according to claim 1; 2,3-diamino-7,8-dihydro-3H-5,8-ethanopyrido-[3,2-d]-pyrimidin-4(6H)-one, compound with platinum chloride (1:1).

* * * * *